(12) United States Patent
Kivioja et al.

(10) Patent No.: US 11,668,005 B2
(45) Date of Patent: Jun. 6, 2023

(54) MANUFACTURING OF COATED ITEMS

(71) Applicant: Picosun Oy, Espoo (FI)

(72) Inventors: Jani Kivioja, Espoo (FI); Marko Pudas, Espoo (FI)

(73) Assignee: PICOSUN OY, Espoo (FI)

( * ) Notice: Subject to any disclaimer, the term of this patent is extended or adjusted under 35 U.S.C. 154(b) by 331 days.

(21) Appl. No.: 16/894,049

(22) Filed: Jun. 5, 2020

(65) Prior Publication Data

US 2020/0385857 A1 Dec. 10, 2020

Related U.S. Application Data

(60) Provisional application No. 62/858,069, filed on Jun. 6, 2019.

(51) Int. Cl.
| | |
|---|---|
| *C23C 16/04* | (2006.01) |
| *A61F 2/90* | (2013.01) |
| *A61M 25/00* | (2006.01) |
| *C23C 16/30* | (2006.01) |
| *C23C 16/34* | (2006.01) |
| *C23C 16/40* | (2006.01) |
| *C23C 16/44* | (2006.01) |
| *C23C 16/455* | (2006.01) |
| *C23C 16/458* | (2006.01) |
| *A61F 2/00* | (2006.01) |

(52) U.S. Cl.
CPC .............. *C23C 16/045* (2013.01); *A61F 2/90* (2013.01); *A61M 25/0009* (2013.01); *C23C 16/308* (2013.01); *C23C 16/34* (2013.01); *C23C 16/405* (2013.01); *C23C 16/4408* (2013.01); *C23C 16/458* (2013.01); *C23C 16/45553* (2013.01); *C23C 16/45555* (2013.01); *A61F 2002/0081* (2013.01); *A61F 2240/001* (2013.01)

(58) Field of Classification Search
CPC .............. C23C 16/045; C23C 16/4408; C23C 16/45525; C23C 16/45555; C23C 16/458
See application file for complete search history.

(56) References Cited

U.S. PATENT DOCUMENTS

| 7,253,424 B2 * | 8/2007 | Murrell ............. H01L 21/67005 |
| | | 250/492.23 |
| 8,211,235 B2 | 7/2012 | Lindfors et al. |
| (Continued) | | |

FOREIGN PATENT DOCUMENTS

| CN | 103924202 A | 7/2014 | |
| WO | WO 2008/118788 A1 * | 10/2008 | ............... B32B 1/00 |
| (Continued) | | | |

OTHER PUBLICATIONS

Alonso-Gonzalez, Leticia, et al., "Three-Dimensional Fully Interlaced Woven Microstrip-Fed Substrate Integrated Waveguide". Progress In Electromagnetics Research, vol. 163, 25-38, 2018.*

(Continued)

*Primary Examiner* — Bret P Chen
(74) *Attorney, Agent, or Firm* — Nixon & Vanderhye

(57) ABSTRACT

A method for manufacturing a coated item 10 in a chemical deposition reactor and a coated item produced by the method are provided. The method includes deposition of a first coating on a first surface of the item 10, and/or deposition of a second coating on a second surface of the item.

14 Claims, 3 Drawing Sheets

(56) References Cited

U.S. PATENT DOCUMENTS

| | | | |
|---|---|---|---|
| 8,272,728 B2* | 9/2012 | Sim | G03B 35/00 347/101 |
| 2004/0142558 A1* | 7/2004 | Granneman | C30B 25/14 118/715 |
| 2007/0241279 A1* | 10/2007 | Starikov | H01L 27/14618 250/338.4 |
| 2008/0299337 A1 | 12/2008 | Glocker et al. | |
| 2011/0009954 A1 | 1/2011 | Cho et al. | |
| 2011/0034993 A1 | 2/2011 | Schwarz et al. | |
| 2012/0004673 A1* | 1/2012 | Noishiki | A61L 27/58 606/151 |
| 2013/0022658 A1* | 1/2013 | Lee | A01N 59/16 424/618 |
| 2015/0337442 A1* | 11/2015 | Agafonov | C23C 16/52 118/695 |
| 2016/0215408 A1* | 7/2016 | Kagajwala | C25D 17/008 |
| 2017/0037509 A1* | 2/2017 | Faguet | B05D 7/22 |
| 2018/0342675 A1* | 11/2018 | Xu | H01L 51/5016 |
| 2022/0235466 A1* | 7/2022 | Pudas | C23C 16/45576 |

FOREIGN PATENT DOCUMENTS

| | | | |
|---|---|---|---|
| WO | 2013/142344 A1 | 9/2013 | |
| WO | WO 2018/189413 A1 * | 10/2018 | C23C 16/455 |

OTHER PUBLICATIONS

Wang, Heyan, et al., "Double-layer interlaced nested multi-ring array metallic mesh for high-performance transparent electromagnetic interference shielding". Optics Letters, vol. 42, No. 8, Apr. 15, 2017, pp. 1620-1623.*

Li, G., et al., "Interlacing method for micro-patterning silver via inkjet printing," SENSORS, 2014 IEEE, 2014, pp. 1687-1690.*

Wu, Lei, et al., "Fabrication of large-area and highly uniform interlaced silicon grating arrays for high-performance SERS substrates". Surfaces and Interfaces 32 (2022) 102156, pp. 1-10.*

Zhou, Wen-Jia, et al., "Electrodeposition and characterization of ordered mesoporous cobalt hydroxide films on different substrates for supercapacitors". Microporous and Mesoporous Materials 117 (2009) 55-60.*

Lin, Jeng-Yu, et al., "Cathodic deposition of interlaced nanosheet-like cobalt sulfide films for high-performance supercapacitors". RSC Advances, 2013, 3, 2043-2048.*

Rikhtegar, Farhad, et al., "Drug deposition in coronary arteries with overlapping drugeluting stents". J Control Release Sep. 28, 2016; 238: 1-9, pp. 1-20.*

Extended European Search Report issued in European Patent Application No. 20178402.2 dated Oct. 21, 2020.

* cited by examiner

MANUFACTURING OF COATED ITEMS

FIELD OF THE INVENTION

The present invention generally relates to manufacturing of coated items by chemical deposition methods. In particular, the invention concerns region-specific deposition of coatings onto interlaced substrates by methods of chemical deposition in vapour phase.

BACKGROUND OF THE INVENTION

Chemical deposition methods, such as Chemical Vapor Deposition (CVD) and Atomic Layer Deposition (ALD), are extensively described in the art. ALD technology generally regarded as a subclass of CVD processes has proved an efficient tool for manufacturing high-quality conformal coatings on three-dimensional substrate structures.

ALD is based on alternating self-saturative surface reactions, wherein different reactants (precursors) provided as molecular compounds or elements in a nonreactive (inert) gaseous carrier are sequentially pulsed into a reaction space accommodating a substrate. Deposition of a reactant is followed by purging the substrate by inert gas. Conventional ALD cycle (a deposition cycle) proceeds in two half-reactions (pulse first precursor—purge; pulse second precursor—purge), whereby a layer of material (a deposition layer) is formed in a self-limiting (self-saturating) manner, typically being 0.05-0.2 nm thick. The cycle is repeated as many times as required for obtaining a film with a predetermined thickness. Typical substrate exposure time for each precursor ranges within 0.01-1 seconds. Common precursors include metal oxides, elemental metals, metal nitrides and metal sulfides.

ALD offers significant benefits in view of capability of the method to generate coatings on complex, multi-element 3D structures or scaffold structure, since precursor molecules distributed in gaseous media reside at all accessible (not-masked) surfaces forming conformal coatings.

However, the same functionality constitutes a significant drawback when applied to formation of region-specific coating layers. For example, traditional chemical deposition methods do not allow producing region-specific (selective) coatings on interlaced structures. Nevertheless, a need for such coatings exists in medical field, for example, in where it would be desirable to obtain implantable intravascular stents (provided as expandable mesh structures) with different material properties for inner and outer surfaces. Traditional ALD methods would inherently produce conformal coatings across all surfaces of such items; thus preventing a manufacturer from producing medical devices with desired properties.

In this regard, an update in the field of vapour-deposition based methods, such as atomic layer deposition technology, is still desired, in view of addressing challenges associated with the application of said methods in manufacturing of three-dimensional interlaced structures with region-specific coatings.

SUMMARY

An objective of the present invention is to solve or to at least alleviate each of the problems arising from the limitations and disadvantages of the related art. The objective is achieved by various embodiments of a method for manufacturing coated interlaced substrates and coated interlaced items produced by said method.

Thereby, in an aspect of the invention, a method for manufacturing a coated interlaced substrate in a chemical deposition reactor, according to what is defined in independent claim 1.

In embodiment, a method for manufacturing a coated interlaced substrate in a chemical deposition reactor is provided, comprising:

obtaining a chemical deposition reactor with a reaction space formed by a reaction chamber and configured to receive, at least in part, a substrate holder made of a fluid-permeable material, onto which an interlaced substrate is mounted such, that a first surface of the substrate faces the reaction space, and a second surface of the substrate is placed against the substrate holder, and in a number of deposition cycles, forming a first coating on the first surface and forming a second coating on the second surface, wherein, each deposition cycle comprises delivering, with a flow of fluid, precursor chemical into the reaction space such, that delivery of at least one precursor chemical into the reaction space occurs via said fluid-permeable material.

In embodiment, the deposition cycle comprises delivering at least two predetermined precursor chemicals into the reaction space, whereby a deposition layer is produced across the first surface of the substrate and/or across the second surface of said substrate.

In embodiment, a first predetermined precursor chemical is delivered into the reaction space via the reaction chamber and a second predetermined precursor chemical, is delivered into the reaction space via the fluid-permeable substrate holder.

In embodiment, the precursor chemicals are delivered into the reaction space in sequential, temporally separated pulses, optionally alternated by purging the reaction space with inert fluid.

In embodiment, delivery of any one of the precursor chemicals into the reaction space is accompanied by generating a counter flow of inert fluid in a direction essentially opposite to the direction of delivery of precursor chemicals into the reaction space.

In embodiment, any one of the first coating and the second coating are formed by the at least one deposition layer deposited across the first surface of the substrate and/or across the second surface of said substrate.

In embodiment, the deposition layers forming the first coating differ from the deposition layers forming the second coating by virtue of at least composition thereof.

In embodiment, formation of the coating on the first and/or the second surfaces is regulated by adjusting pressure of fluid flowing into the reaction space via the reaction chamber and/or via the fluid-permeable substrate holder.

In embodiment, the substrate holder is made of a fluid-permeable material selected from the group consisting of porous metal, porous ceramics and porous polymer.

In embodiment, the substrate holder has an essentially hollow interior, into which said at least one precursor chemical is received. In embodiment, the substrate holder is an essentially tubular structure.

In embodiment, the interlaced substrate is an essentially tubular structure formed by a mesh or a web.

In embodiment, the interlaced substrate is an implantable medical device, such as a stent or a catheter, or forms a part of such device.

In embodiment, the coating is deposited onto the interlaced substrate with Atomic Layer Deposition (ALD).

In another aspect, a coated item in the form of an interlaced structure is provided according to what is defined in the independent claim 15.

In another aspect, a coated implantable medical device is provided according to what is defined in the independent claim 16.

in embodiment, said coated implantable medical device is configured as an interlaced structure, comprising a first coating on a first surface and/or a second coating on a second surface, wherein the first coating and the second coating differ from one another by virtue of at least composition thereof.

In embodiment, the first surface is an exterior surface of the implantable medical device and the second surface is an interior surface, respectively.

In embodiment, the coated implantable medical device is a stent, such as an expandable stent, or a catheter.

The utility of the present invention arises from a variety of reasons depending on each particular embodiment thereof. Deposition layers (atomic layers or films) deposited by ALD methods are pinhole-free and fully conformal, therefore, the ALD technology has a high potential in manufacturing of high-quality coatings required for various applications, in particular, medical applications. The method disclosed hereby thus allows for rendering selective surfaces of an exemplary interlaced structure (a scaffold-like structure) with different surface chemistries and regions-specific properties, such as ability to attract/repel water, ability to bind other molecules, and the like. Hence, by the method disclosed hereby, particular surface regions (e.g. internal and external surfaces) of the interlaced structures, such as, such as implantable (intra)vascular stents or catheters, can be rendered with distinct physicochemical and/or biological functions.

The method further allows for selective preventing or sustaining material deposition, such as ALD deposition, for example, on any one of the surfaces (inner or outer) of the exemplary essentially tubular medical device, such as a stent or a catheter.

In addition to coating of the aforesaid implantable items, the method disclosed hereby is fully applicable for depositing region-specific coatings on any essentially interlaced structures with or without essentially tubular configuration. Hence, coating of essentially planar interlaced structures is not excluded.

In the present disclosure, materials with a layer thickness below 1 micrometer (μm) are referred to as "thin films".

In the context of present disclosure, the term ALD comprises all applicable ALD based techniques and any equivalent or closely related technologies, such as, for example the following ALD sub-types: plasma-assisted ALD, PEALD (Plasma Enhanced Atomic Layer Deposition) and photon-enhanced Atomic Layer Deposition (known also as photo-ALD or flash enhanced ALD).

The expression "a number of" refers herein to any positive integer starting from one (1), e.g. to one, two, or three; whereas the expression "a plurality of" refers herein to any positive integer starting from two (2), e.g. to two, three, or four.

The terms "first" and "second" are not intended to denote any order, quantity, or importance, but rather are used to merely distinguish one element from another.

BRIEF DESCRIPTION OF THE DRAWINGS

The invention will now be described, by way of example only, with reference to the accompanying drawings, in which.

DETAILED DESCRIPTION OF THE EMBODIMENTS

Figure 2:
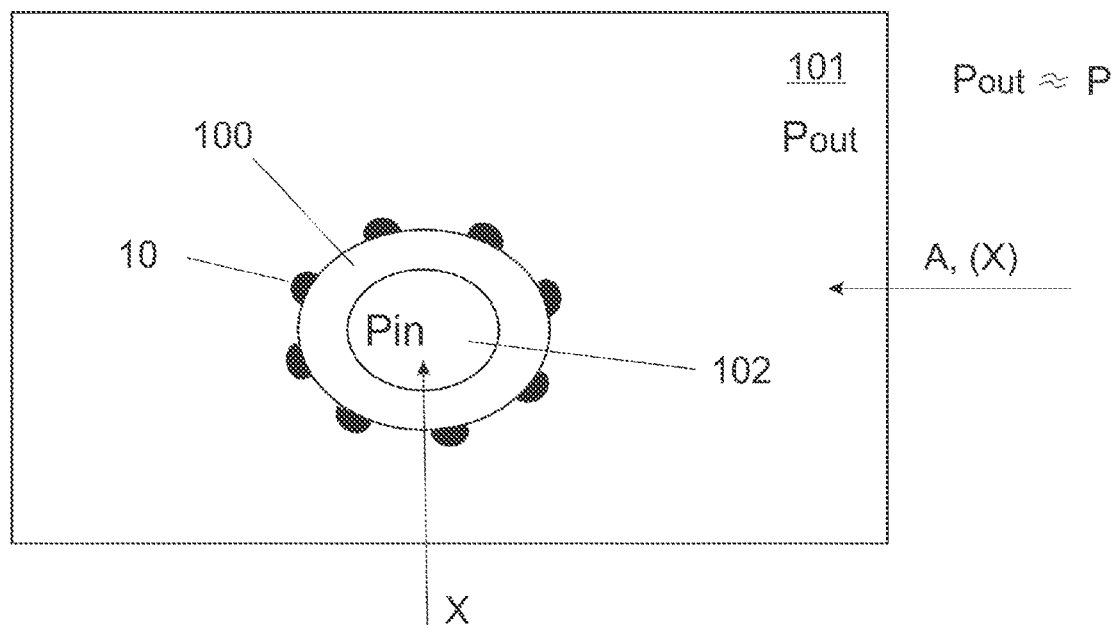
FIGS. 2 and 3 show a method for manufacturing a coated interlaced substrate 10, according to the embodiments.
Figure 2:
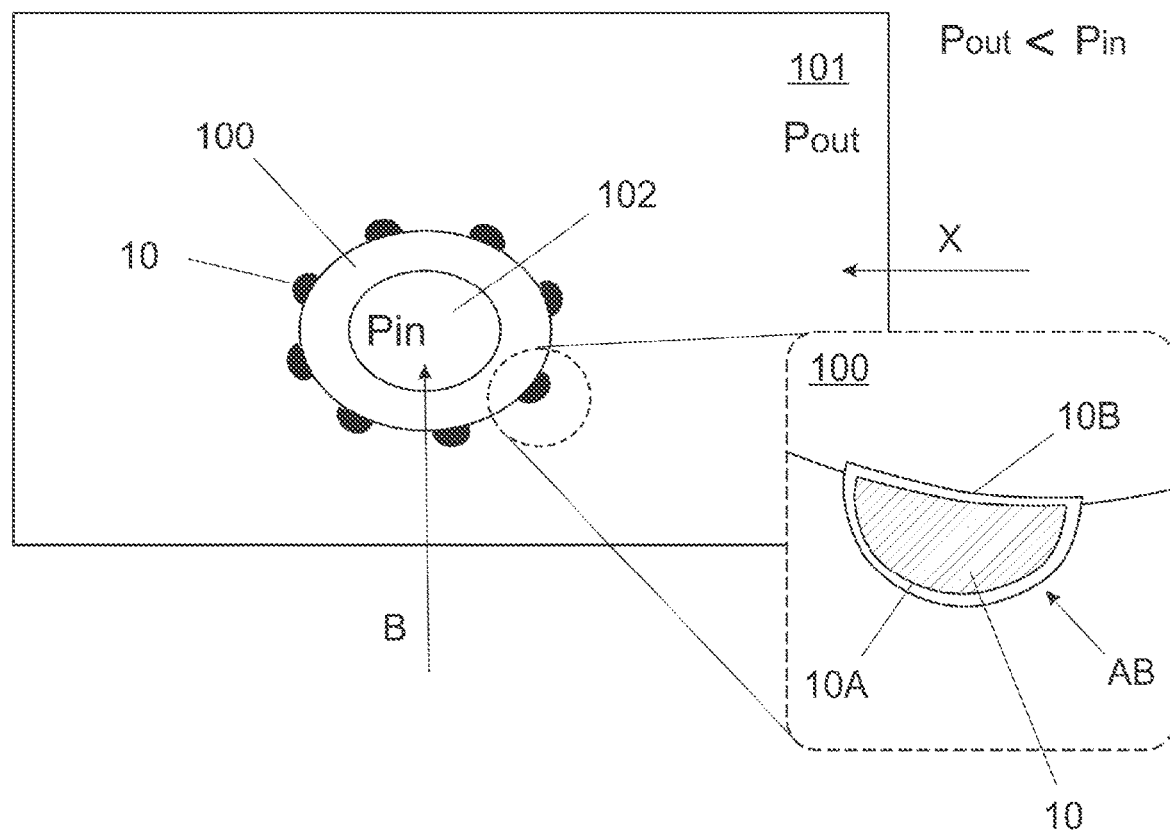
Figure 3:
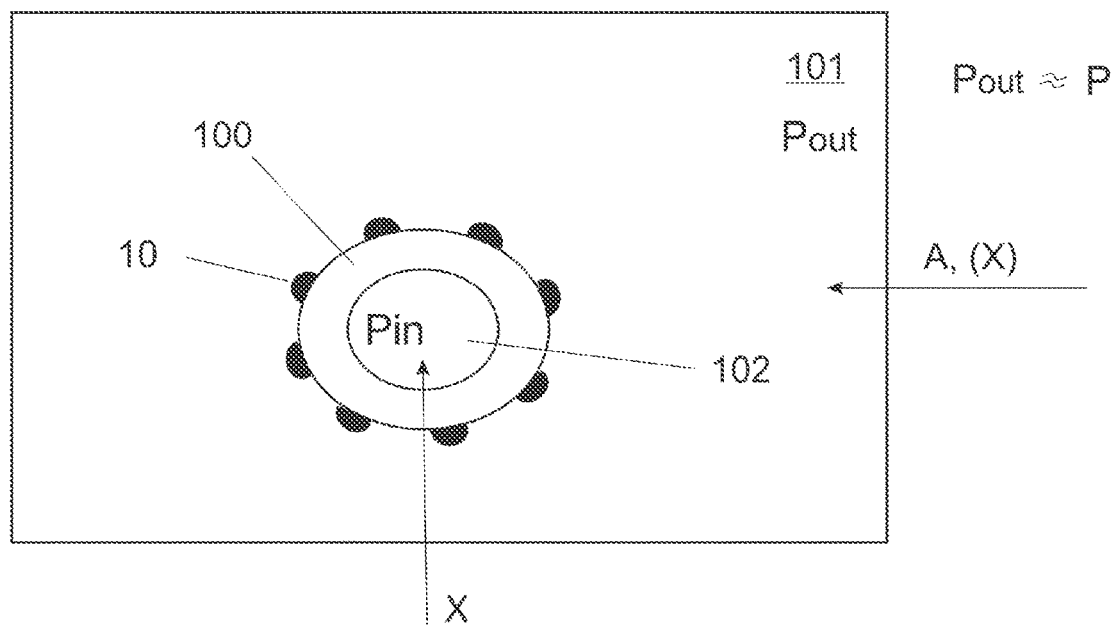
Figure 3:
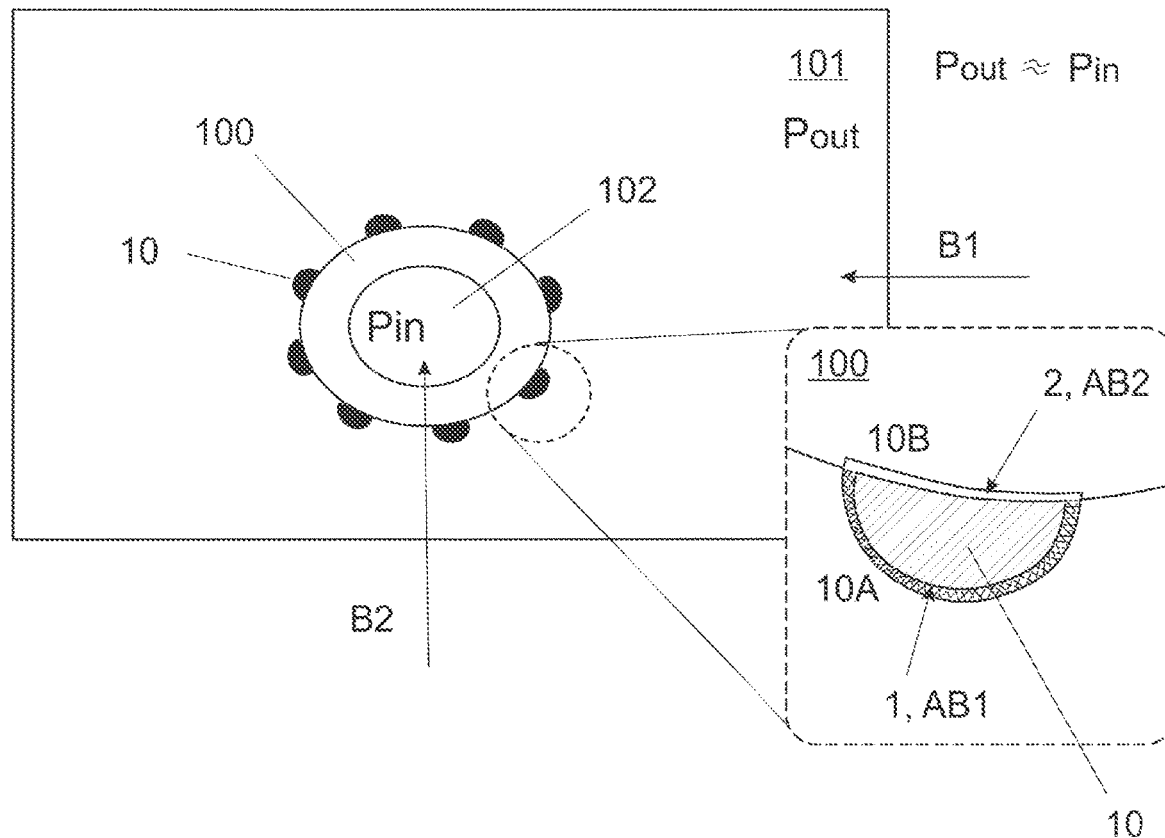

FIGS. 2 and 3 illustrate a method for manufacturing a coated interlaced substrate in a chemical deposition reactor.

The interlaced substrate 10 to be coated comprises a first surface 10A and a second surface 10B. Coating process is implemented in an exemplary chemical deposition reactor comprising a reaction chamber 101 with a reaction space (deposition space) established by an interior of said reaction chamber 101.

The reactor is configured to exploit principles of vapor-deposition based techniques, such as Atomic Layer Deposition (ALD).

The basics of ALD growth mechanism are known to a skilled person. ALD is a chemical deposition method based on sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness. In some instances, Chemical Vapour Deposition (CVD) may be utilized.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: MLD (Molecular Layer Deposition), plasma-assisted ALD, PEALD (Plasma Enhanced Atomic Layer Deposition) and photon-enhanced Atomic Layer Deposition (known also as photo-ALD or flash enhanced ALD).

A basic ALD deposition cycle, resulting in deposition of a deposition layer (atomic layer), consists of four sequential steps: pulse A, purge A, pulse B and purge B. Pulse A consists of a first precursor fluid and pulse B of another precursor fluid. Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapor pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

In terms of an overall implementation, the deposition reactor may be based on an ALD installation described in the U.S. Pat. No. 8,211,235 (Lindfors), for example, or on the installation trademarked as Picosun R-200 Advanced ALD system available from Picosun Oy, Finland. Nevertheless, the features underlying a concept of the present invention can be incorporated into any other chemical deposition reactor embodied as an ALD, MLD or CVD device, for example, or any subtype thereof.

The reaction chamber can be configured as an open-top vessel sealed with a lid (not shown). Such type of a reactor has an essentially circular layout when viewed from the top. In some instances, the reaction chamber can be configured as a vessel loadable from side or from the bottom (not shown). In such configurations the lid is configured as a hatch disposed laterally (within a sidewall) or at the bottom of the reactor vessel. Such type of reaction chambers may have a crossflow blown from the side, for example.

The reactor further comprises a number of appliances configured to mediate a flow of fluids into the reaction space 101 (the reaction chamber). Mentioned appliances are provided as a number of intake lines (hereafter, feedlines) and associated switching and/or regulating valves (not shown).

The reactor further comprises an evacuation line (not shown) for discharging an exhaust flow, such as excess carrier, precursor and reaction products, out of the reaction chamber. The evacuation line constitutes a fore-line for an evacuation pump unit and it may comprise, in some configurations, a closing valve, preferably upstream the pump unit. It is preferred that withdrawal of fluidic substance from the reaction chamber is implemented in an uninterrupted manner, whereby the pump unit, preferably configured as a vacuum pump, removes fluidic substance from the reaction chamber continuously during the entire deposition process.

The interlaced substrate 10 is mounted onto a substrate holder 100, such that its first surface 10A faces the reaction space 101 and its second surface 10B is placed against the substrate holder 100.

The interlaced substrate 10 can be provided in the form of a mesh or a web, such as a wire mesh, for example, optionally an expandable wire mesh.

Figure 1:
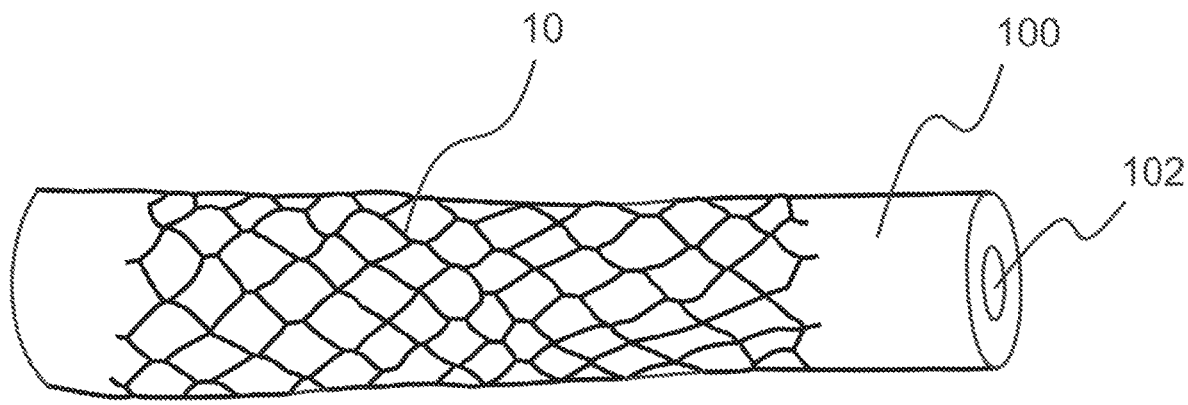
FIG. 1 shows an interlaced substrate 10 mounted on a substrate holder 100.

The interlaced substrate 10 can be configured as an essentially tubular, pipe-like structure (see FIG. 1). Alternatively, the interlaced substrate 10 can be configured as an essentially flat, planar structure (not shown).

In embodiments, the interlaced substrate 10 is an implantable medical device, such as a stent or a catheter. An exemplary configuration includes an expandable, mesh-wire type vascular stent. Alternatively, the substrate 10 forms at least a part of said medical device.

In some configurations, the substrate holder 100 can be disposed essentially between the reaction chamber and any feedline (or a related appliance for directing precursor fluids into the reaction space). In some instances, the substrate holder 100 is received, at least partly, into the reaction chamber. For example, the substrate holder can be placed between the feedline and the reaction chamber such, that only a portion of said substrate holder (with the substrate 10 mounted thereto) is received into the reaction space, unless partial coating (e.g. lengthwise) of the substrate item is desired.

The substrate holder 100 can be further positioned, at least partly, inside a feedline or form, at least partly, a part of the feedline.

The substrate holder 100 is preferably made of an essentially fluid-permeable material, such as porous material, that enables unhindered fluid flow therethrough. The substrate holder can thus form a fluid-permeable passageway for precursor fluids entering the reaction space. In some configurations, the substrate holder 100 is positioned such that fluids, flowing via the feedline(s) into the reaction space 101, can enter said reaction space only by penetrating through the fluid-permeable material forming said holder of made of.

In some configurations (FIG. 1) the substrate holder 100 is an essentially tubular structure, onto which the interlaced substrate item 10 can be mounted. The substrate holder 100 can be provided as an essentially solid (without internal apertures and/or channels) piece made of fluid-permeable material. In some instances, it is preferred that the holder 100 has an essentially hollow interior 102, in the form of a through-channel or a blind-end channel, for example.

In terms of its structure, the substrate holder 100 includes all kinds of essentially tubular, channel-like shapes that enable uniform flow across their entire surfaces to attain the effect described herein below.

The fluid-permeable material that constitutes the substrate holder 100 can be represented by any one of the porous metal, porous ceramics or porous polymer, including silicone polymer. Other materials, such as porous composites and semiconductor materials (e.g. silicon) are not excluded.

The substrate holder 100 can be further configured as a fork- or rake-like arrangement with a common base portion and a number of protrusions/protruding "fingers" onto which the substrate items 10 to be coated can be mounted (not shown). The base portion of such holder can be made hollow and connected to a feedline or feedlines. The substrate holder for essentially flat, planar substrate items 10 can be implemented based on a similar principle.

Additionally or alternatively, a number of substrate holders can be placed into the reaction space 101.

In exemplary configurations, position of the substrate holder 100 with regard to the reaction chamber is such, that fluids directed into the reactive space 101 via the feedlines, for example, enter the reaction space 101 via the fluid-permeable material.

Precursor fluid(s) is/are delivered inside the reaction space 101 by means of at least one feedline connectable to a container with a precursor chemical.

To incorporate a number of individual substrate holders configured as fluid-permeable passageways, the reactor can comprise two, three or more feedlines and a corresponding number of inlets. The reactor can comprise as many feedlines and associated inlets as considered feasible in terms of the deposition process and the apparatus design. One or more such feedlines can be connected directly to the substrate holder 100, to feed fluids there into.

In other configurations (in particular, in case of providing support for multiple substrate items 10; the rake-like arrangement), the substrate holder 100 can be placed inside the reaction chamber and connected to the feedline(s) via its base portion.

Precursor chemicals are delivered into the reaction space 101 (via feedlines) in a fluidic form. Precursor fluid delivered into the reaction space 101 is a gaseous substance comprising a predetermined precursor chemical A, B, B1, B2 (FIGS. 2, 3) carried by an inert carrier. Whether the precursor is inherently provided in a gaseous form (e.g. $NH_3$, or $O_2$), dilution of such precursor with a carrier fluid may not be required. Carrier fluid without the precursor chemical is indicated on FIGS. 2 and 3 by a character X.

Precursor chemicals are supplied into the reaction space from a supply source or sources configured as containers, cartridges or a piping system, for example (not shown). Each source preferably contains a predetermined precursor species A, B, B1, B2 provided as a chemical compound, a molecule, or an element. Each source is equipped with at least one valve, provided as a manual closing valve, for example. A variety of precursor chemicals required for deposition reaction(s), such as ALD reaction(s), can be directed into the reaction space via a single feedline.

As mentioned above, precursor(s) can be provided in a gaseous form, such as ammonia gas ($NH_3$) or oxygen gas ($O_2$), which may be modified at least partly to ozone ($O_3$) by an appropriate equipment, such as ozone generator (not shown). Additionally or alternatively, precursor(s) can be provided in liquid or solid forms and vaporized prior to being admixed to the inert carrier.

Inert carrier X is a fluid, preferably gas, such as nitrogen ($N_2$), argon (Ar) or any other suitable gaseous medium that possesses essentially zero reactivity towards the precursors (reactants) and the reaction products. Inert carrier gas X is supplied from a separate source or sources (not shown).

The method disclosed hereby involves a number of deposition cycles, whereupon a first coating 1 is formed on the first surface 10A of the substrate and a second coating 2 is formed on the second surface 10B of the substrate (FIG. 3). During each deposition cycle, a number of precursor species are delivered into the reaction space resulting in formation of a deposition layer (an atomic layer), whereas production of a coating 10A, 10B comprises depositing at least one, but typically more than one deposition layer onto the substrate.

Each deposition cycle comprises delivering, with a flow of fluid, precursor chemicals into the reaction space 101 such, that delivery of at least one precursor chemical into the reaction space 101 occurs via the fluid-permeable material the substrate holder 100 is made of.

In embodiments, the deposition cycle comprises delivering at least two predetermined precursor chemicals into the reaction space 101, whereby a deposition layer produced across the first surface 10A of the substrate 10 and/or across the second surface 10B of said substrate.

Delivery of said at least two predetermined precursor chemicals is implemented such that the first precursor chemical enters into the reaction space 101 via the reaction chamber (and a corresponding feedline or feedlines, not shown), whereas the second precursor chemical is directed into said reaction space 101 via the fluid-permeable substrate holder 100.

In embodiments, the deposition layers forming the first coating 1 differ from the deposition layers forming the second coating 2 by virtue of at least composition thereof, thus rendering the coated surfaces by distinct surface chemistry. Other differentiating factors include, but are not limited to thickness and density of the final coating films, ability to attract and repel water molecules, as well as any other chemical, physical- and/or biological property. Biological properties can include e.g. specific responses at a substrate—(biological) host interface, an ability of not having toxic or injurious effects on biological systems, an ability to act as a suitable implantable material, an antimicrobial activity, and the like.

Fluidic flow through the essentially fluid-permeable material 100 can be controlled by pressure difference generated across said material with the evacuation pump and a number of regulating devices, such as switch valves equipped with mass-flow controller(s) and/or gas flow meter(s), for example. Other control means include conventional appliances, such as gas- and pressure sensors. The chemical deposition reactor advantageously comprises an (automated) control system, implemented as a computer unit, for example, and comprising at least one processor and a memory with an appropriate computer program or software.

By adjusting pressure difference generated across the essentially fluid-permeable substrate walls, formation of coating(s) 1, 2 with varying composition and/or other properties can, in turn, be regulated. By regulating pressure difference, velocity of fluid flowing into the reaction space 101 via the reaction chamber ($P_{out}$) and via the fluid-permeable substrate holder ($P_{in}$) can be adjusted.

In embodiments, the coating(s) 1, 2 is/are deposited onto the interlaced substrate 10 with Atomic Layer Deposition (ALD).

Various ways of implementing the method shall be presented hereinbelow in a number of non-limiting examples.

Example 1. Installation and Assembly

An interlaced substrate 10 is obtained in the form of a stent device provided in the form of an essentially tubular, scaffold mesh-type structure. The stent can be configured as an implantable device, such as a self-expandable metallic stent. The stent has an outer surface 10A and an inner surface 10B. The stent 10 is positioned onto/around the fluid-permeable substrate holder 100 such, that its first surface 10A faces the reaction space 101 and its second surface is placed against the substrate holder (FIG. 1).

The fluid-permeable substrate holder is made of a porous material that enables unrestricted flow of fluids, such as gaseous media, therethrough. Hereby, the fluid-permeable substrate holder 100 can be configured as an essentially tubular inlet comprising the hollow interior 102.

The substrate holder 100 with the stent 10 mounted thereon, as shown on FIG. 1, is placed into the reaction space 101 formed by a reaction chamber of an exemplary ALD reactor. By the way of example, the installation R-200 Advanced ALD system available from Picosun Oy, Finland, can be utilized. The holder 100 is connected to a feedline or feedlines (the feedline is not shown). When fluid is directed into the reaction chamber via the feedline(s) connected to the holder 100, fluid enters the reaction space 101 essentially through the fluid-permeable material said holder is made of.

The reactor further comprises at least one feedline through which fluid(s) are delivered into the reaction space. Such feedline(s) is/are not connected to the substrate holder 100.

Fluid flow into the reaction space 101 through the feedline (s), onto which the substrate holder 100 is mounted or incorporated, and through the interior 102 of said substrate holder is further referred to as a flow from the "inside" ("in"), whereas fluid flow directly entering the reaction space (via feedline(s) provided with the reaction space 101, but not shown with regard to the holder 100) is referred to as a flow from the "outside" ("out").

The flow from the interior side 102 of the tubular substrate holder 100 to the reaction space 101 through the essentially fluid-permeable material (100) can be controlled by adjusting pressure difference ($P_{in}/P_{out}$) generated across the essentially fluid-permeable substrate walls. By regulating pressure difference, velocity of fluids flowing across the fluid-permeable wall (in both in- and out-directions) can be adjusted.

Fluidic flow through the essentially fluid-permeable material 100 can be controlled by pressure difference generated across said material an evacuation pump provided in chemical deposition reactor and regulating devices, as described herein above.

When $P_{in}$ exceeds $P_{out}$, fluidic flow occurs from the interior side 102 of the substrate holder 100 towards the reaction space 101. When $P_{in}$ approximately equals to $P_{out}$, fluid flow rate through the fluid-permeable wall (100) is close to diffusive. Thus, setting the flow rate for two distinct precursor fluids (viz. fluids containing distinct precursor chemicals) flowing across the fluid-permeable wall in both directions (from "Out" to "In" and from "In" to "Out") to very low allows for obtaining distinct coatings 1 and 2 on the outer- and inner surfaces 10A, 10B, respectively. The flow rate regarded as very low is equal to or less than 10 sccm, preferably, equal to or less than 1 sccm, still preferably, equal to or less than 0.1 sccm. Sccm refers to standard cubic centimeters per minute; $cm^3/min$ in standard conditions for temperature and pressure of the fluid, wherein said standard temperature is 0 deg C. (273 K) and standard pressure is 1 atm).

Example 2. Deposition of the Interlaced Substrate 10 with a Coating

1a) Introduce inert carrier fluid X, such as nitrogen gas ($N_2$), into the reaction space 101 via the reaction chamber and, optionally, via the feedline connected to the tubular substrate holder 100. Upon stabilization of the flow (0.1-100 s, preferably, 1 s), add precursor A, such as titanium tetrachloride ($TiCl_4$), for example, to the "external" flow (delivered via the reaction chamber) carried by the inert carrier X. By adjusting pressure settings (hereby, $P_{out}$ approximately equals $P_{in}$), the entire surface of the interlaced substrate (10A and 10B) shall be saturated with molecules A (FIG. 2, upper box).

1 b) Purge by directing inert fluid X into the reaction space via the reaction chamber and, optionally, via the feedline connected to the substrate holder 100. Purge duration 1-100 s, preferably, 10 s.

2b) Deliver a second precursor B, such as ammonia gas ($NH_3$) into the reaction space via the feedline connected to the tubular substrate holder 100, while directing the inert carrier X ($N_2$) into the reaction chamber. By adjusting the pressure such that $P_{in}$ exceeds $P_{out}$ ($P_{in} \gg P_{out}$), precursor B is forced to penetrate through the fluid-permeable wall 100 and reside onto both surfaces 10A and 10B of the interlaced substrate 10. The precursor B enters chemical reaction with precursor A thus forming a deposition layer AB, hereby, titanium nitride (TiN), on both exterior- and interior surfaces 10A and 10B, respectively (FIG. 2, lower box).

2b) Purge (same as 1a).

Repeat the deposition cycle (steps 1a, 1b, 2a and 2b) n times until the coating of desired thickness is attained. The coating can comprise at least one deposition layer AB or a "stack" of identical deposition layers AB.

Example 3. Deposition of the Exterior- and Interior (10A, 10B) Surfaces of the Interlaced Substrate 10 with Coatings 1, 2 Having Distinct Surface Chemistry 1a) Same as step 1a in Example 2 (FIG. 3, upper box). Conformal deposition of the precursor A, hereby, $TiCl_4$, for example, onto the entire substrate 10 (surfaces 10A, 10B).

1 b) Purge.

2a) Introduction of two different precursors B1 and B2. Deliver a precursor chemical B1, such as ozone ($O_3$) or water vapor ($H_2O$) into the reaction space 101 via the reaction chamber and deliver another precursor chemical B2, such as ammonia gas ($NH_3$) into the reaction space via the feedline connected to the tubular substrate holder 100. By maintaining $P_{in}$ approximately equal to $P_{out}$, different chemical reactions A+B1 and A+B2 can be conducted at the outer- (10A) and inner- (10B) surfaces of the substrate 10, respectively. The procedure allows for producing a deposition layer AB1 (hereby, titanium oxide, $TiO_n$) on the exterior surface 10A along with producing a deposition layer AB2 (hereby, titanium nitride, TiN) on the interior surface 10B of the substrate (FIG. 3, lower box).

The precursors B1 and B2 can be delivered into the reactions space simultaneously or one by one. In the latter case, delivery of the precursor fluid is accompanied by delivery of the carrier fluid X from the opposite side (not shown). For example, delivery of precursor B1 into the reaction chamber is accompanied by guiding inert fluid X through the substrate holder 100; whereas delivery of B2 into the reaction space 101 through the substrate holder 100 is accompanied by guiding inert fluid X into the reaction chamber.

2b) Purge.

3) Optional. Use any suitable precursor (e.g. B3, not shown), which is known to react differently with B1 compared to B2, for selectively coating only one surface (10A or 10B) of the substrate.

Repeat the deposition cycle (steps 1a, 1 b, 2a, 2b and, optionally, 3) n times until the coating of desired thickness is attained. By the method, homogenous coatings $(AB1)_n$, $(AB2)_n$ (n=a number of deposition cycles) of varying thickness can be deposited on any one of the surfaces 10A, 10B, by "stacking" deposition layers AB1 on the outer surface 10A, while maintaining the flow of inert fluid through the interior 102 of the substrate holder 100 (or vice versa). Thus, the outer surface 10A can be deposited with a 1 nm coating (1), whereas the inner surface—with a 0.5 nm coating (2), for example.

In fact, when the precursor B1 ($O_3$) enters chemical reaction with precursor A ($TiCl_4$) on the outer surface 10A, an atomic layer of titanium oxynitride ($TiO_xN_y$) can be formed on the outer surface 10A. Thus, production of the coating 1 consisting of titanium (di)oxide may require saturation of the reaction space 101 with ozone molecules in a number of subsequent pulses.

The procedure allows for production of coatings 1, 2 with different surface chemistries and/or rendered with different physical, chemical and/or biological properties at each surface 10A, 10B. Each coating 1, 2 thus comprises at least one deposition layer AB1, AB2.

Example 4. Production of Multilayer Coatings I

This example essentially combines the procedures disclosed in Examples 2 and 3.

At first, the entire substrate 10 can be deposited with an at least one deposition layer AB (e.g. TiN), in a manner shown on FIG. 2 (Example 2). Thereafter, the procedure according to the Example 3 (FIG. 3) can be applied to establish at least one deposition layer AB1 (e.g. $TiO_2$) on the outer substrate surface 10A or on the inner surface 10B.

Deposition series "AB (conformal, surfaces 10A, 10B)+ AB1 (surface 10A)" and/or "AB+AB2 (surface 10B)" and/or "AB+AB1 and AB2" can be repeated n times as desired to produce heterogeneous coatings with uniform thickness across the substrate 10 or thickness varying for surfaces 10A and 10B. In the example, the coating 1 (surface 10A) can comprise deposition layers $(AB)_n$ and $(AB1)_n$, whereas the coating 2 (surface 10B) can comprise deposition layers $(AB)_n$ and $(AB2)_n$.

Example 5. Production of Multilayer Coatings II

To obtain coatings 1, 2 with distinct composition (e.g. $TiO_2$ and TiN) from at least one common precursor, such as $TiC_{14}$, for example, the procedure can be further implemented as follows.

1a) Introduce inert carrier fluid X, such as nitrogen gas ($N_2$), into the reaction space 101 via the reaction chamber and, optionally, via the feedline connected to the tubular substrate holder 100. Upon stabilization of the flow (0.1-100 s, preferably, 1 s) pulse a (common) precursor A (e.g. $TiCl_4$) into the reaction space 101 via the reaction chamber (not through the substrate holder), while preserving the flow of inert carrier X through the substrate holder ($P_{in}$ exceeds $P_{out}$). Due to the counterflow established by the inert carrier X through said substrate holder, the precursor A ($TiCl_4$) cannot reach the inner surface 10B of the substrate 10, which faces the fluid-permeable holder 100.

1b) Purge.

2a) Direct precursor B1 (e.g. $H_2O$) into the reaction space 101 via the reaction chamber (not through the substrate holder), while maintaining the counterflow of inert carrier X through the substrate holder, whereby the deposition layer AB1 ($TiO_2$) is generated on the outer surface 10A. The inner surface 10B remains uncoated.

2b) Purge.

3a) Conformal deposition of the precursor A ($TiCl_4$) onto the entire substrate (surfaces 10A, 10B). The common precursor ($TiCl_4$), is pulsed into the reaction space 101 via the reaction chamber again; however, this time with no hindrance (counterflow) from the inside of the substrate holder 100 ($P_{out}$ approximately equals $P_{in}$) thus enabling saturation of the entire substrate surface with molecules A (in similar manner as shown in Examples 2 and 3, steps 1a). It should be noted, that in this case, the precursor A is deposited, at the outer surface 10A, onto the previously deposited layer AB1.

3b) Purge

4a) Deliver precursor B (e.g. $HN_3$) into the reaction space 101 via the reaction chamber in similar manner as for step 3a. In such a case, conformal growth of the deposition layer AB can be attained for the entire substrate.

Alternatively, delivery of the precursor B into the reaction space can be optionally accompanied by re-establishing the inert counterflow (X) through the substrate holder 100. Inert counterflow can be established if growth of the deposition layer AB (TiN) is desired only for the outer surface 10A.

4b) Purge.

Procedure allows for conducting deposition series "AB1 (surface 10A)+AB (conformal, surfaces 10A, 10B)" and/or "AB1 (surface 10A)+AB (only for the surface 10A)". The latter option is obtainable in condition that the counterflow is established from the interior 102 of the substrate holder 100 at step 4a.

The deposition cycles 1-2 and 3-4 can be repeated n times. As result, the substrate 10 is rendered with surfaces 10A, 10B with different properties, attainable, in this Example, by regulating the inert counterflow X from the interior 102 of the substrate holder 100.

Hence, in some embodiments, delivery of any one of the precursor chemicals into the reaction space 101 is accompanied by generating a counter flow of inert fluid in a direction essentially opposite to the direction of delivery of precursor chemicals into the reaction space 101.

The method further allows for selective deposition of coatings on one of the surfaces 10A or 10B, while deposition on the other surface can be sustained or prevented.

In still another example, a hydrophobic precursor, such as tridecafluoro-1,1,2,2-tetrahydrooctylmethyl-bis(dimethylamino)silane (also known as FOMB(DMA)S or $C_8F_{13}H_4$ $(CH_3)Si(N(CH_3)_2)_2$), can be used as precursor A to be deposited conformally on all surfaces of the substrate 10, in a manner described hereinabove. After purge, any suitable precursor B can be delivered into the reaction space 101 via the reaction chamber, while maintaining pressure difference across the interior and exterior surfaces of the fluid-permeable substrate holder 100 such, that said second precursor B does not penetrate inside the substrate holder (hereby, $P_{in}$>$P_{out}$) and reacts with precursor A only at the outer surface 10A. Region-specific coating can be attained by establishing the inert counterflow through the substrate holder 100 in a manner described hereinabove. Deposition cycles can be repeated n times until the coating (1, 2) with desired thickness is obtained. As a consequence, only the inner surface 10B of the tubular substrate 10, such as stent, shall be deposited with the hydrophobic film.

In all embodiments, the precursor chemicals (e.g. A, B, B1, B2) are delivered into the reaction space 101 in sequential, temporally separated pulses. In most instances, the reaction space is purged with inert fluid X after each precursor pulse. Inert fluid X can be guided into the reaction chamber via any feedline or feedlines including the feedline(s) connected to the substrate holder 100.

In a latter case, purging of the fluid-permeable material occurs in direction from the interior 102 of the substrate holder towards the reaction space 101. Thus, once the reaction chamber is clear of gaseous reactants, it is still desired to purge the fluid-permeable substrate holder 100. Purging the substrate holder 100 generally requires more time than purging the reaction space 101, due to slower penetration of fluids through the fluid-permeable material. In such as case, purging can be a process, in where reverse flow of inert fluid (e.g. $N_2$) is established, thereupon fluid from the reaction space is sucked into the tube-shaped substrate holder through the porous walls. Purging said tubular substrate holder can be faster, if the substrate holder is configured as a through-pipe. Reverse flow can be regulated by a valve provided on an appropriate feedline (not shown).

For those skilled in the art it is clear that the precursors described hereinabove to deposit the coatings 1, 2 (e.g. TiN, $TiO_n$) are mere examples of compounds, which can be established, by ALD methods, from a metal-containing precursor ($TiCl_4$) and secondary chemicals, such as gases ($NH_3$, $O_3$/$H_2O$). Nevertheless, any compound suitable for establishing a chemical reaction by ALD or CVD methods can be utilized within the concept of the present invention.

Hence, the coatings 1, 2 can be established from a metal-containing precursor (A) and at least two non-similar gaseous substances (B1, B2). In some other instances, the coatings 1, 2 can be established from a number of metal-containing precursors. Utilization of various compounds (oxides, nitrides sulfides, etc.) that comprise elements other than metal, such as silicon dioxide, $SiO_2$, for example, is also not excluded.

Non-limiting examples for the coatings 1, 2 include aluminium oxide ($Al_2O_3$), zinc oxide (ZnO), or a combination thereof. These materials are biocompatible and dissolve in controllable manner when in contact with bodily fluids, thus enabling production of implantable devices for controlled drug release.

In an aspect, a coated item 10 configured as an interlaced structure is provided, said item comprises a first coating 1 on a first surface 10A and a second coating 2 on a second surface 10B, wherein the first coating 1 and the second coating 2 differ from one another by virtue of at least composition thereof. The coated item can be configured as an implantable device, such as a stent, e.g. a vascular stent, or a catheter.

In further aspect, an implantable medical device 10 is provided configured as an interlaced structure that comprises a first coating 1 on a first surface 10A and a second coating 2 on a second surface 10B, wherein the first coating 1 and the second coating 2 differ from one another by virtue of at least composition thereof.

In embodiments, the coated implantable medical device 10 is a stent or a catheter.

It shall be appreciated by those skilled in the art that the embodiments set forth in the present disclosure may be adapted and combined as desired. The disclosure is thus intended to encompass any possible modifications of the deposition method, recognizable by those of ordinary skill in the art, within a scope of appended claims.

The invention claimed is:

1. A method for manufacturing a coated interlaced substrate in a chemical deposition reactor, comprising:
    obtaining a chemical deposition reactor with a reaction space formed by a reaction chamber and configured to receive, at least in part, a substrate holder made of a fluid-permeable material, onto which an interlaced substrate is mounted such that a first surface of the substrate faces the reaction space, and a second surface of the substrate is placed against the substrate holder, and
    in a number of deposition cycles, forming a first coating on the first surface and/or forming a second coating on the second surface,
    wherein, each deposition cycle comprises delivering, with a flow of fluid, a precursor chemical into the reaction space such that delivery of at least one precursor chemical into the reaction space occurs via said fluid-permeable material.

2. The method of claim 1, wherein the substrate holder has an essentially hollow interior, into which said at least one precursor chemical is received.

3. The method of claim 1, wherein each deposition cycle comprises delivering at least two predetermined precursor chemicals into the reaction space, whereby a deposition layer is produced across the first surface of the substrate and/or across the second surface of said substrate.

4. The method of claim 1, in which a first predetermined precursor chemical is delivered into the reaction space via the reaction chamber and a second predetermined precursor chemical is delivered into the reaction space via the fluid-permeable substrate holder.

5. The method of claim 1, in which the precursor chemicals are delivered into the reaction space in sequential, temporally separated pulses, optionally alternated by purging the reaction space with inert fluid.

6. The method of claim 1, in which delivery of any one of the precursor chemicals into the reaction space is accompanied by generating a counter flow of inert fluid in a direction essentially opposite to the direction of delivery of precursor chemicals into the reaction space.

7. The method of claim 1, wherein any one of the first coating and the second coating are formed by at least one deposition layer deposited across the first surface of the substrate and/or across the second surface of said substrate.

8. The method of claim 1, wherein deposition layers forming the first coating differ from deposition layers forming the second coating by virtue of at least composition thereof.

9. The method of claim 1, wherein selective formation of the coating on the first surface and/or on the second surface is regulated by adjusting pressure of fluid flowing into the reaction space via the reaction chamber and/or via the fluid-permeable substrate holder.

10. The method of claim 1, wherein the substrate holder is made of a fluid-permeable material selected from the group consisting of porous metal, porous ceramics and porous polymer.

11. The method of claim 1, wherein the substrate holder is an essentially tubular structure.

12. The method of claim 1, wherein the interlaced substrate is an essentially tubular structure formed by a mesh or a web.

13. The method of claim 1, wherein the interlaced substrate is an implantable medical device or forms a part of such device.

14. The method of claim 1, wherein the coating is deposited onto the interlaced substrate with Atomic Layer Deposition (ALD).

* * * * *